United States Patent [19]

Feingers et al.

[11] 4,301,139

[45] Nov. 17, 1981

[54] MULTILAYER COLUMN CHROMATOGRAPHY SPECIFIC BINDING ASSAY METHOD, TEST DEVICE AND TEST KIT

[75] Inventors: Judith Feingers; Anthony J. Pick; Daniel B. Wagner, all of Jerusalem, Israel

[73] Assignee: Ames-Yissum Ltd., Jerusalem, Israel

[21] Appl. No.: 50,543

[22] Filed: Jun. 21, 1979

[51] Int. Cl.$^3$ .................... G01N 33/48; B01N 23/10; B65D 7/00

[52] U.S. Cl. .................... 424/1; 23/230 B; 210/264; 210/284; 422/61; 424/8; 424/12

[58] Field of Search .................... 422/61; 23/230 B; 424/1, 8, 12; 210/264, 284

[56] References Cited

U.S. PATENT DOCUMENTS

| | | | |
|---|---|---|---|
| 4,094,647 | 6/1978 | Deutsch et al. | 424/1 |
| 4,168,146 | 9/1979 | Grubb et al. | 23/230 B |
| 4,189,304 | 2/1980 | Adams, Jr. et al. | 23/230 B |
| 4,205,058 | 5/1980 | Wagner et al. | 424/12 |

*Primary Examiner*—Benjamin R. Padgett
*Assistant Examiner*—Christine M. Nucker

*Attorney, Agent, or Firm*—Andrew L. Klawitter

[57] ABSTRACT

A specific binding assay method, and a test device and test kit for use therein, for determining a liqand, such as an antigen or antibody, in, or the ligand binding capacity of, a liquid medium, particularly a body fluid such as serum, wherein the unknown ligand competes with a labeled component, such as a radiolabeled form of the ligand or of a binding analog of the ligand, for binding with a binding partner, and wherein separation of the resulting bound-species and free-species of the labeled component is accomplished by allowing the liquid reaction mixture to be drawn by capillary action into a column comprising a bed of an adsorbent material selective for one of the two species. The improvement comprises using a column containing at least one additional bed of capillarily absorbent material disposed above said adsorbent bed and which is substantially nonadsorbent relative to the one of said two species which said adsorbent bed selectively binds. The use of specific types of capillarily absorbent beds in addition to the selectively adsorbent bed to form multilayer columns overcomes several unforeseen problems encountered in using the previously known column chromatography method for certain assay applications.

37 Claims, 5 Drawing Figures

MULTILAYER COLUMN CHROMATOGRAPHY SPECIFIC BINDING ASSAY METHOD, TEST DEVICE AND TEST KIT

BACKGROUND OF THE INVENTION

1. Field of the Invention

This invention relates to the quantitative determination of substances in or characteristics of liquid media, including body fluids such as serum, based on specific binding assay techniques. In particular, the invention is directed to the detection of antigens or haptens based on immunoassay techniques involving the use of labeled reagents, such as radiolabeled reagents. The present invention provides an improved method of performing the separation of bound- and free-label inherent in heterogeneous specific binding assays.

2. Description of the Prior Art

A living system is able to detect, recognize and respond to the presence of foreign material (antigen) such as protein, virus, bacteria, and so forth, within that system. This response takes, inter alia, the form of producing an antibody specific for the particular antigen. There then occurs a specific reaction between the antibody and the antigen to form a complex. An antibody once produced is also capable of binding a hapten, i.e., a relatively small and simple compound which may be the determinant group of a given antigen, which hapten is capable of binding with the specific antibody but incapable itself of giving rise to the production of an antibody, unless it is bound to an antigenic carrier.

The binding interaction between an antigen or a hapten and its antibody is specific and sensitive. Other types of materials that participate in similar specific and sensitive binding interactions are enzymes and their substrates; materials such as hormones, vitamins, metabolites and pharmacological agents, and their receptors and binding substances; and other substances known in the science. These specific and sensitive binding reactions have given rise to a rapidly emerging analytical technique known as the specific binding assay technique. In one such type of assay method, the substance, or group of substances, to be determined (herein referred to as "ligand") in a liquid sample is placed in competition with a labeled form of the ligand or of a binding analog thereof for binding to a binding reagent. Where a radioactive label is used and the binding reagent is an antibody, the method is known as a radioimmunoassay method. Recently, several alternative labeling materials have been reported for replacement of radioisotopes, including enzymes, coenzymes, enzyme substrates, enzyme modulators such as inhibitors and allosteric effectors, fluorescent molecules, luminescent molecules, and others. For illustrative purposes, the discussion which follows describes one particular type of specific binding assay technique, a competitive binding radioimmunoassay technique.

This system consists of antigen or hapten labeled with a radioactive marker, unlabeled native antigen (in the test sample) and specific antibody whereby there is competition between the unlabeled antigen and the labeled antigen for binding to a limited amount of antibody. Hence, the greater the concentration of unlabeled antigen from the test sample in the system, the less the labeled antigen will be bound by the antibody. This may be diagrammatically represented as follows:

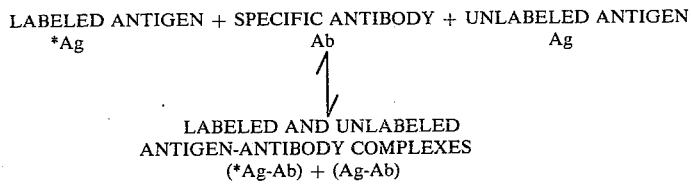

LABELED ANTIGEN + SPECIFIC ANTIBODY + UNLABELED ANTIGEN
*Ag           Ab           Ag

LABELED AND UNLABELED
ANTIGEN-ANTIBODY COMPLEXES
(*Ag-Ab) + (Ag-Ab)

If the concentration of labeled antigen and antibody is fixed and the only variable is the level of unlabeled antigen, it becomes possible to establish an assay system for measuring the unknown level of unlabeled antigen by physically separating the antigen-antibody complex from the remaining free antigen (both labeled and unlabeled). The radioactivity of the unknowns is compared with a standard curve plotting of the values given by a range of known amounts of the antigen treated in the same manner.

The need for a simple and reliable method for accomplishing the essential separation of the bound- and free-species of the labeled component in heterogeneous specific binding assays has been felt for many years, ever since the analytical value of such assays was fully realized. Numerous separation techniques have evolved including chromatoelectrophoresis, a cumbersome technique; ascending paper-wick chromatography [Scand. J. Clin. Lab. Invest. 20:297(1967)], a limited and commercially unattractive technique; precipitation of the antigen-antibody complex, a technique requiring the use of a centrifuge and which in some cases yields variable results due to the lack of selectivity in the precipitating agents available; the double-antibody technique, requiring an additional antibody reagent and additional incubation time; and the use of solid phase binders, such as solid phase antibodies and various adsorbents, all of which have left room for improvement.

Recently, there has been developed a novel separation technique referred to as the ascending column chromatography technique which is described in U.S. Pat. No. 4,205,058 and assigned to the instant assignee. In accordance with this new method, the bound-species and free-species of the labeled component are separated by contacting at least a portion of the binding reaction mixture, a predetermined time after its formation, with a column comprising an adsorbent material which is both selective for binding one of said bound- and free-species and capillarily absorbent relative to said reaction mixture whereby said reaction mixture is drawn into the column by capillary action and said bound- and free-species are separated along the column. This technique provided for the first time a practical, fast and reliable method of separation which is effected passively, without any significant care required of the technician performing the assay. After incubation of the binding reaction mixture, the technician simply places an adsorbent column in contact with the mixture and waits until the mixture has been drawn into the column, at which time separation is inherently accomplished by the selective binding capacity of the adsorbent. The adsorbed species is held at the beginning portion of the column, while the nonadsorbed species is transported by capillary migration of the liquid carrier toward the other end of the column. The label, usually a radioactive material, can then be measured in one or the other of the separated species by measurement at the beginning portion or terminal portion of the column.

While in principle the ascending column chromatography technique is applicable to the determination of any ligand in, or any ligand binding capacity of, a liquid medium, certain unforeseen difficulties have been encountered in some applications of the technique. For example, since it is most desirable to achieve as great and sharp a spatial separation of the bound- and free-species as possible along the column, it is generally desirable to select an adsorbent whose affinity for binding one of such species (in practice, usually the free-species) is quite high. However, it has been unexpectedly found that sometimes this affinity can be so high that it creates a competition between the ligand binding agents present in the reaction mixture and the adsorbent for binding of the ligand. As a result, the complexes of labeled and unlabeled ligand or binding analog bound to binding agent which had formed during the binding reaction are dissociated and the released labeled material, converted into a free-species of the labeled component, becomes adsorbed to the column material. As this process occurs during the capillary migration of the reaction mixture along the column, there results a "trailing" of labeled component along the column, thereby reducing the sensitivity and reproducibility of the assay. Such trailing effect is particularly troublesome where radiolabels are used and no radiopaque shield is used in measuring the label in one of the separated species as described in the aforementioned U.S. patent application. Other difficulties encountered in certain applications of the previously described ascending column chromatography technique to which the present invention is addressed are discussed in the disclosure to follow.

It is, therefore, a principal object of the present invention to provide an improved specific binding assay of the above-described "ascending column chromatography" type, wherein the above described undesirable phenomenon of "trailing" of labeled material along the column is eliminated so as to afford a sharper and better separation between the bound- and free-species. It is a further object of the invention to provide a specific binding assay method of the above-mentioned type wherein, for a given reaction system involving a particular ligand and its binding partner, the selectively adsorbent material may be chosen from a broader range of materials, including those which hitherto have been excluded from use in the known ascending column chromatography technique because of excessive affinity for either the ligand or its binding partner. Yet another object of the invention is to provide an ascending column chromatography specific binding assay which permits the use of considerably smaller amounts of the selectively adsorbent material, the cost of which is, in some cases, an important factor in determining the practical and commerical application of the method.

SUMMARY OF THE INVENTION

Accordingly, the present invention provides, in a specific binding assay method for determining a ligand in, or the ligand binding capacity of, a liquid medium, wherein for determining said ligand, said liquid medium is combined with assay reagent means comprising (i) as a labeled component, said ligand or a binding analog thereof incorporated with a label and (ii) a binding reagent for said ligand; or wherein for determining the ligand binding capacity of said liquid medium suspected of containing a binding agent for said ligand, said liquid medium is combined with assay reagent means comprising, as a labeled component, said ligand or a binding analog thereof incorporated with a label, thereby to form a binding reaction mixture having a bound-species as said labeled component bound to said binding reagent and a free-species as said labeled component not bound to said binding agent;

wherein said bound-species and said free-species of said labeled component are separated by contacting at least a portion of said binding reaction mixture, a predetermined time after formation thereof, with a column comprising a bed of an adsorbent material which is both (a) selective for binding one of said bound-species and free-species and (b) capillarily absorbent relative to said reaction mixture, whereby said at least a portion of said reaction mixture is drawn into said column by capillary action and said bound-species and said free-species are separated along said column; and wherein said label is measured in one of the separated species;

the improvement wherein said column comprises at least one additional bed of material which is capillarily absorbent relative to said reaction mixture, such additional bed being disposed in said column in contact with the end of said adsorbent bed opposite that which is contacted with said reaction mixture, and said additional bed material being substantially nonadsorbent relative to the one of said bound-species and free-species which said adsorbent bed selectively binds.

Thus, it can be seen that, in accordance with the present invention, as the reaction mixture is carried by capillary action through the column the adsorbed species is retained entirely within that portion of the column comprising the bed of adsorbent material, while the nonadsorbed species is transported inertly, i.e., without the possibility of trailing, away from the adsorbent bed portion of the column. As a consequence, the separation between the bound- and free-species is optimal.

The additional, nonadsorbent bed provided by the present invention serves as a sort of "capillary pump" to transport the nonadsorbed species away from the adsorbent bed. The capillary pump bed is preferably nonadsorbent for both of the bound- and free-species, but for certain applications may be adsorbent for the one of the bound- and free-species which the adsorbent bed does not selectively bind. Also, where the capillary pump bed is essentially nonadsorbent for either species, as is preferred, the column may comprise a further additional bed of material which is capillarily absorbent relative to said reaction mixture, such further additional bed being disposed in said column in contact with the end of said substantially nonadsorbent bed opposite that which is in contact with said adsorbent bed, and said further additional bed material being adsorbent for the one of said bound-species and free-species which said adsorbent bed does not selectively bind. This further additional bed serves as a sort of "trapping" bed for the nonadsorbed species and, as will be described more fully hereinbelow, eliminates backflow of the nonadsorbed species in those applications wherein such is found to be a problem.

Therefore, the present invention provides a specific binding assay method which retains and improves upon the great advantages of the ascending column chromatography method, namely, that the necessary separation step is reduced to the simple task of contacting the reaction mixture with the column for a sufficient period of time to permit the necessary absorption of the liquid into the column; that the column resulting upon completion of the test, carrying the separated bound- and free-species, is convenient for subsequent measuring steps, particularly where the label is radioactive; that the mechanical steps of initiating the separation step and removing the separation device to a measuring location are readily adaptable to automation; and that when the label used is of a hazardous type, such as a radioactive label, all of the label added in forming the reaction mixture ends up in a single, readily disposable device - the column.

DESCRIPTION OF THE PREFERRED EMBODIMENTS

Figure 1:
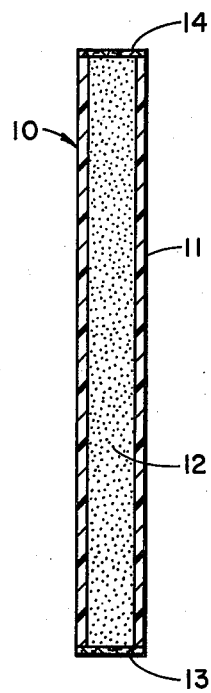
FIG. 1 is a longitudinal cross-sectional view of a typical known ascending chromatography separation test device.

In the context of this disclosure, the following terms shall be defined as follows: "ligand" is the substance, or class of related substances, whose presence or the amount thereof in a liquid medium is to be determined; "binding agent for the ligand" is any substance, or class of substances, which has a specific binding affinity for the ligand to the exclusion of other substances; and "binding analog of the ligand" is any substance, or class of substances, which behaves essentially the same as the ligand with respect to the binding affinity of the binding agent for the ligand.

LIGAND

It is contemplated that the present assay may be applied to the detection of any ligand for which there is a specific binding partner and, conversely, to the detection of the capacity of a liquid medium to bind any such ligand (usually due to the presence of a binding partner or agent for the ligand in the medium). The ligand usually is a peptide, protein, carbohydrate, glycoprotein, steroid, or other organic molecule for which a specific binding partner exists in biological systems or can be synthesized. The ligand, in functional terms, is usually selected from the group consisting of antigens and antibodies thereto; haptens and antibodies thereto; and hormones, vitamins, metabolites and pharmacological agents, and their receptors and binding substances. Examples of ligands are immunologically-active polypeptides and proteins of molecular weights between 1,000 and 4,000,000, such as antibodies and antigenic polypeptides and proteins, as well as haptens of molecular weights between 100 and 1,500. Representative of such antigenic polypeptides are angiotension I and II, C-peptide, oxytocin, vasopressin, neurophysin, gastrin, secretin, and glucagon. Representative of antigenic proteins are insulin, chorionic gonadotropin (e.g., HCG), carcinoembryonic antigen (CEA), myoglobin, hemoglobin, follicle stimulating hormone, human growth hormone, thyroid stimulating hormone (TSH), human placental lactogen, thyroxine binding globulin (TBG), intrinsic factor, transcobalamin, enzymes such as alkaline phosphatase and lactic dehydrogenase, and hepatitis associated antigens. Representative of antibody ligands are those antibodies of the IgG, IgE, IgM and IgA classes specific for any of the antigens or haptens, or a class thereof, herein described. The class of hapten ligands is exemplified by thyroxine ($T_4$), triiodothyronine ($T_3$), the estrogens such as estriol, prostaglandins, vitamins such as biotin, vitamin $B_{12}$, folic acid, vitamin E, vitamin A, and ascorbic acid (vitamin C), and drugs such as carbamazepine, quinidine, digoxin, digitoxin, theophylline, phenobarbital, primidone, diphenylhydantoin, morphine, nicotine, and so forth.

Certain liquid media contain a binding agent for the ligand, and the ligand binding capacity of such media may also be determined for any of the ligands contemplated above. For example, ligands which appear in body fluids such as blood oftentimes have an associated carrier such as a globulin which serves as a natural transport for the ligand. An example is the association of the thyroid hormones $T_4$ and $T_3$ with thyroxine binding globulin (TBG). As is well known, a clinically useful assay is the determination of serum binding capacity for such hormones, particularly $T_3$.

ADSORBENT BED

As described in the aforementioned U.S. Pat. No. 4,205,058, since numerous adsorbents selective for one of the bound- and free-species are well documented in the literature, it is not necessary to set forth an exhaustive list here. The adsorbent bed usually is homogeneous throughout its volume, consisting of a single type of capillarily absorbent, particulate material having the desired selective adsorptivity, however, it is within the scope of this invention to employ adsorbent beds of various and heterogeneous characters where desired for a particular application. For example, where the adsorbent material chosen as the most desirable because of its binding selectivity is itself not capillarily absorbent, an appropriately absorbent bed can be produced by mixing such adsorbent material with an inert, capillarily absorbent material, such as those to be described in detail below. Particularly useful adsorbents have been found to include cross-linked polyvinyl alcohol, cross-linked dextrans, starch, and silica gel. These adsorbents are appropriately hydrophilic and stable in aqueous reaction mixtures, and can be selected to preferentially adsorb the free-species of commonly performed binding assays.

"CAPILLARY PUMP" BED

As in the case of the adsorbent bed, the capillary pump bed usually is homogeneous throughout its volume, consisting of a single type of capillarily absorbent, particulate material having substantially no adsorptive affinity for either of the bound- and free-species. However, for this bed to serve its function as a capillary pump, its character can be varied quite widely. For particular applications it may be heterogeneous in composition and have various adsorptive properties so long as it does not have any substantial adsorptive capacity for the one of the bound- and free-species which the adsorbent bed selectively binds. As will be shown in the illustrations to follow, the capillary pump bed may even have an affinity for the other of the bound- and free-species which the adsorbent bed does not bind or may consist of multiple layers of different capillarily adsorbent materials. The exact nature and composition of this bed is not critical so long as it serves its basic function as a capillary pump as herein described. Particularly useful materials for the capillary pump bed are purified fine sand, glass powder (usually from 100–200 mesh) and flint powders of the type conventionally used for grinding glass. Other materials suitable for the intended purpose will be evident to those of ordinary skill in the art.

OTHER COLUMN PARAMETERS AND EMBODIMENTS

The test device, i.e., the column separation device, for use in the present assay method, in general, comprises firstly an elongated tube, usually constructed of a plastic material, which is transparent to the detectable characteristic of the label by which it is measured in the course of the assay. Thus, if the detectable characteristic of the label is radioactivity, then the tube is radiotransparent but otherwise could be light opaque. Similarly, if the detectable characteristic is spectrophotometric, such as light production or a color change, then the tube is light transparent. One end of the tube, namely that end designed to be contacted with the reaction mixture in conducting the assay, is covered or sealed with liquid permeable retainer means such as a filter paper disc glued or otherwise fixed to the tube opening. Other forms of such retainer means will be evident to those working in the art. This retainer means serves to support the separation column itself which is contained within the tube and in contact with such retainer means. According to the present invention, the column comprises (i) a first bed of capillarily absorbent material disposed adjacent to said retainer means and selectively adsorbent for one of the bound-species and free-species and (ii) at least one additional bed of capillarily absorbent material disposed in contact with the end of said first bed opposite that which is adjacent to said retainer means and substantially nonadsorbent relative to the one of said bound-species and free-species which said first bed selectively binds.

Preferably, the column completely, or nearly completely, fills the tube and the end of the tube opposite that covered by the liquid permeable retainer means is covered by gas permeable retainer means to hold the column within the tube during transport, storage and use and which allows, during use, the escape of air which is displaced by capillary absorption of the reaction liquid into the column. This avoids creation of an atmospheric backpressure which otherwise might lessen or stop altogether the capillary advance of the reaction liquid. Such gas permeable retainer means oftentimes will be identical to that used as the liquid permeable retainer means, e.g., a filter paper disc affixed to the tube opening.

For certain applications, it may be desirable to include in the column a further additional bed of material to serve as a "trapping" bed or layer to prevent backflow. Such trapping bed is capillarily absorbent relative to the reaction mixture, of course, since it constitutes a part of the overall column. It is disposed in the column in contact with the end of the capillary pump bed and is adsorbent for the one of the bound- and free-species which the adsorbent bed does not selectively bind. Such trapping bed, therefore, serves a primary function to trap or bind the nonadsorbed species carried away from the adsorbent bed by capillary flow. It has been found that upon standing after complete absorption of the reaction mixture into the column, there can be a tendency in certain assays for the nonadsorbed labeled species to migrate by diffusion back towards the adsorbent bed. To overcome this back flow, the use of an appropriate trapping bed or layer is valuable. The trapping bed need not exhibit any discriminating type of adsorption with respect to the bound- and free-species, although at a minimum it should be adsorptive for the nonadsorbed species carried up the column. Thus, it can be generally adsorptive and of a type capable of indiscriminately binding both species since in the operation of the assay substantially only the nonadsorbed species reaches it by capillary migration. Thus, the trapping bed can be composed of such adsorbents as crosslinked polyvinyl alcohol, silica gel, and cellulosic materials.

Also, where the column is composed of packed particulate beds, as is usual, there is a tendency for the column to settle during transport and storage. Thus, there can be advantageously provided, on top of the column (usually on top of the capillary pump bed) between the column and the above-described gas permeable retainer means, a comparatively thin layer of a soft, compressible material, e.g., cotton, wool or sawdust. This layer forms a kind of elastic plug interposed between the upper end of the column and the gas permeable retainer means, and exerts a constant compression force on the column thereby preventing the formation therein of cracks or voids due to settling of the column materials upon storage or transport. In some cases this compression function and that of the trapping bed or layer can be served by the same material or mixture, and therefore a single additional bed or layer performs a dual purpose in constructing the test device.

In a preferred embodiment, the test device also comprises an indicator composition incorporated in at least a minor portion of the column at the end thereof opposite that which is adjacent the liquid permeable retainer means, i.e., at the terminal end of the column relative to the advance of the liquid reaction mixture absorbed thereinto. Such indicator composition is selected to provide a detectable response, such as a color change, upon contact with the reaction mixture to signal completion of capillary absorption thereof into the column. This assures the user that the separation function has been accomplished and permits the earliest possible reading of the test. Numerous possible indicator compisitions will be evident, such as the use of moisture sensitive indicators and pH sensitive chromogens that change color upon contact with the reaction mixture which usually has a given buffered pH.

Preferably, the total volume of capillarily absorbent beds or layers in the column is sufficiently large to allow capillary absorption of all of the reaction mixture. Also, separation of the bound- and free-species can be enhanced after all the reaction mixture has been drawn into said column by contacting the lower end of said column with a volume of liquid inert with respect to the selective adsorption of said one of said bound-species and said free-species by said adsorbent bed and allowing said inert liquid to be drawn into said column by capillary action.

Further details relating to the general operation of the present invention are available from the teachings of U.S. Pat. No. 4,305,058 referred to hereinabove. In particular, such U.S. patent describes various methods for measuring the label in one of the separated species (e.g., where the label is radioactive, with or without the use of a radiopaque shield) and various methods of plotting standard curves for use in assaying unknowns.

Now with reference to the drawings, FIG. 1 depicts a typical example of the previously known ascending chromatography column test device as described in the aforementioned U.S. Pat. No. 4,305,058. Test device 10 comprises a tube 11 which is entirely filled with a capillarily absorbent, selectively adsorbent material forming bed 12 which is held between liquid permeable retainer means 13 and gas permeable retainer means 14. In operation, retainer means 13 is contacted with the binding reaction mixture, initiating capillary absorption thereof upwards through bed 12. The free-species (in these illustrations for simplicity sake it will be assumed that it is the free-species which the adsorbent bed 12 selectively binds) is bound by the adsorbent bed 12 as soon as it contacts available binding sites, whereas the bound-species travels upward, unaffected by the adsorbent, along with the capillarily advancing reaction mixture. Thus, the entire free-species becomes bound at the lower or intake portion of bed 12 with the bound-species distributed along the column above such portion. Separation is enhanced by subsequent contact of retainer means 13 with a volume of liquid which does not affect the adsorption of the free-species and which is capable of being capillarily absorbed into the column. Upon such absorption, the bound-species is pushed further up the column and thus farther away from the free-species. Selective measurement of one of the separated species is then made as described previously.

Figure 2:
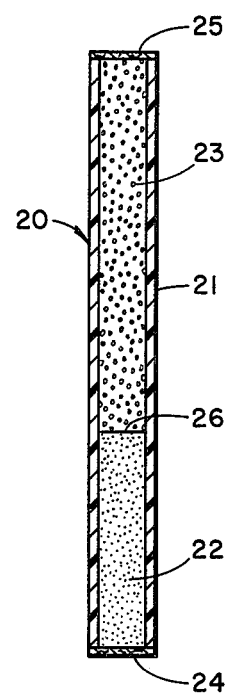
FIGS. 2-4 are longitudinal cross-sectional views of three illustrative embodiments of the improved separation test device of the present invention.

The most basic form of the present test device is depicted in FIG. 2. In this fundamental embodiment, the test device 20 comprises a tube 21 packed with two separate and distinct beds or layers 22 and 23 held between liquid permeable retainer means 24 and gas permeable retainer means 25. Adsorbent bed 22 is adjacent retainer means 23 and nonadsorbent, capillary pump bed 23 is superimposed on bed 22. Bed 23 is capillarily absorbent but, according to a preferred embodiment of the present invention, is substantially nonadsorbent for the free-species.

At this point it should be recalled that if in using known test device 10 the affinity of the adsorbent for the free-species is so great that it strips labeled component from the binding agent, thereby transforming bound-species into free-species as the reaction mixture flows upward in the column, free-species becomes adsorbed to some degree along the whole length of the column above that lower portion wherein the free-species from the binding reaction is concentrated. This results in the disadvantageous "trailing" phenomenon. The construction of test device 20 (FIG. 2) overcomes such problem, since above the boundary line 26 between adsorbent bed 22 and nonadsorbent, capillary pump bed 23, no adsorbent for the free-species is present and accordingly there is no force tending to strip free-species from the bound-species. Thus, the bound-species is carried inertly away from adsorbed bed 22 with no possibility of trailing.

Figure 3:
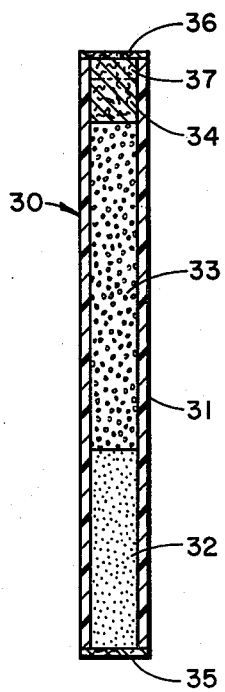

A preferred variation of the present test device is shown in FIG. 3 of the drawings. Here, test device 30 comprises a tube 31 containing a three-layered column consisting of adsorbent bed 32, capillary pump bed 33 and bed or layer 34 composed of a compressible material to form a sort of mechanical spring to preserve the structural integrity of the overall column held between retainer means 35 and 36. The upper portion 37 of bed 34, which constitutes the uppermost and a minor portion of the overall column, is incorporated with an indicator composition as previously described which provides a detectable response, such as a color change, when contacted with the reaction mixture. Thus, when the rising front of the reaction mixture is finally brought by capillary absorption up the column to the indicator incorporated portion 37, the detectable response is elicited, signaling completion of capillary absorption of the reaction mixture into the column.

Alternatively, bed 34 may be composed of an adsorbent for the bound-species to trap same so as to prevent backflow of such species down the column after separation. This trapping bed 34 might also be compressible, thereby serving two functions. Obviously, the relative sizes of the various beds 32, 33 and 34 can be altered over a wide range to accomplish optimal separation of bound- and free-species. The proportions shown in the figures are illustrative only and do not imply that any particular bed is required to be larger or smaller in volume than any other bed.

Figure 4:
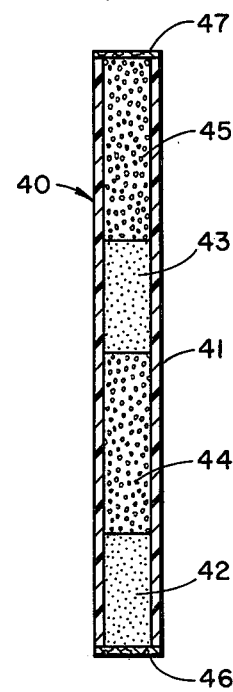

FIG. 4 depicts a further contemplated embodiment with test device 40 comprising a tube 41 containing two adsorbent beds 42 and 43 and two capillary pump beds 44 and 45 held between retainer means 46 and 47. This device is intended for use in detecting two different ligands in a test sample. In such an assay, the test sample is combined with reagents comprising labeled forms of each of the two ligands and different binding agents for each ligand. Thus, as a result of the binding reaction, two free-species and two bound-species are formed. Adsorbent bed 42 is selected to be adsorbent for one free-species only and bed 43 adsorbent for the other free-species. Both bound-species are carried away into bed 45 allowing selective measurement of the separated free-species in adsorbent beds 42 and 43, respectively. In this embodiment, considering bed 42 to be adsorbent for one free-species, the remaining portion of the column, namely the composite of beds 43, 44 and 45, is substantially nonadsorbent for such free-species and thus essentially constitutes, as a unit, a capillary pump bed similar to bed 23 in FIG. 2.

It is obvious to formulate numerous variations of the combinations illustrated in FIGS. 2–4 and such are considered to be within the scope of the present invention.

LABEL

In principle, the label may be any of those known in the art or hereafter conceived for use in specific binding assays; however, it is most advantageous to use a label which can be measured while within the column without removal of some or all of its contents. In such a condition, the tube holding the column is transparent to the labeling characteristic. Such characteristics may be color, light production, or radio-activity, the latter being preferred in view of the current state of the art. Gamma-emitting radioisotopes such as $^{125}I$, $^{131}I$ and $^{57}Co$ are especially useful labels. The present invention provides a separation device well suited to radioassays, since the column test device itself can be used in the measurement step and provides, upon completion of the assay, a disposable device containing all of the radioactivity introduced to the test sample. Physical contact between the technician and radioactive material is minimized in the disposal operation.

TEST KIT

To provide an integral, mercantile combination, the present invention takes the form of a test kit comprising all of the essential elements, and optional elements where desired, for performing the improved assay method. Such test kit comprises a packaged combination of a container for containers holding the essential reagent or reagents along with the novel test device described in detail hereinabove. Thus, a test kit for determining a ligand in a liquid medium comprises, in addition to the separation test device, one or more containers holding (1) said ligand or a binding analog thereof incorporated with a label, and (2) a binding agent for said ligand. For determining the ligand binding capacity of a liquid medium the test kit would comprise a container of said ligand or a binding analog thereof incorporated with a label and the separation test device. Of course, additional reagents as are known in the art and which may be desirable from a commercial and user standpoint, such as buffers, diluents, standards, and so forth, can be included in the test kit either in mixture with one or more of the essential assay reagents or in separate containers.

The present invention will now be illustrated, but is not intended to be limited, by the following examples:

PREPARATION OF TEST DEVICES

Plastic tubes about 9 centimeters (cm) long and about 0.7 cm inner diameter were used. A disc of Whatman 41 filter paper (obtained from Whatman, Inc., Clifton, New Jersey USA), having the same diameter as the outer diameter of the tube, was glued to the bottom of each tube to serve as liquid permeable retainer means. The tube was then filled with a dry, particulate selectively adsorbent material to a height of $1.6 \pm 0.1$ cm. The remaining part of the tube, except for a few millimeters (mm) at its top, was filled with a dry, particulate, inert hydrophilic powder, about 100–200 mesh [approximately 2 grams (g) per tube]. The top part of the tube was then filled with ordinary sawdust to form a compressive layer of about 3–4 mm, and thereafter a second disc of Whatman 41 filter paper was glued to the top end of the tube to serve as gas permeable retainer means.

EXAMPLE 1

Radioimmunoassay for Thyroid Stimulating Hormone (TSH)

Test devices were prepared as described above using silica gel 60 powder, 230–400 mesh (particle size 0.04–0.0063 mm; obtained from E. Merck, Darmstadt, West Germany) as the selective adsorbent in the lower layer and fine purified sand (100–200 mesh) as the inert particulate filler material ("capillary pump" bed).

In order to perform a radioimmunoassay for TSH, the following reagents, all dissolved in phosphate buffer, pH 7.8, were added to test tubes:
1. 100 microliters ($\mu$l) of serum or TSH standards [the standards were diluted with phosphate buffer containing 2% bovine serum albumin (BSA) and 1% polyvinylpyrrolidone (PVP)].
2. 50 $\mu$l of anti-TSH antibody dissolved in phosphate buffer (pH 7.8) containing human chlorionic gonadotropin, ethylendiamine-tetraacetic acid and BSA.

The test tubes were gently shaken to ensure thorough mixing of the reagents and were allowed to incubate at room temperature for 16 hours.

50 $\mu$l of $^{125}$I-TSH [about 20–50 thousand counts per minute (kcpm)] were then added to each test tube, followed by gentle shaking and incubation at 37° C. for 2 hours.

A silica/sand column test device was then placed in each test tube with the end thereof enclosing the silica gel bed immersed in the reaction mixture at the bottom of the test tube. When all the reaction mixture had been absorbed by the column, the total radioactivity of the test tube including the column was measured to determine a "total count".

Phosphate buffer (600 $\mu$l) containing 20% BSA was then added to each test tube and allowed to be absorbed by the column. Thereafter the test tube including the column was inserted into the well of a gamma-counter and the radioactivity of the intake portion of each column was selectively measured to determine a "partial count" for each column. The values of the total count and partial count were measured in a sample, and the corresponding values, measured in a reference standard containing no TSH, were used to calculate the ratio of percent bound (sample) to percent bound (standard zero):

$$\%B/B_o = \frac{\text{(total count - partial count) of sample}}{\text{(total count - partial count) of "standard zero"}} \times 100$$

Figure 5:
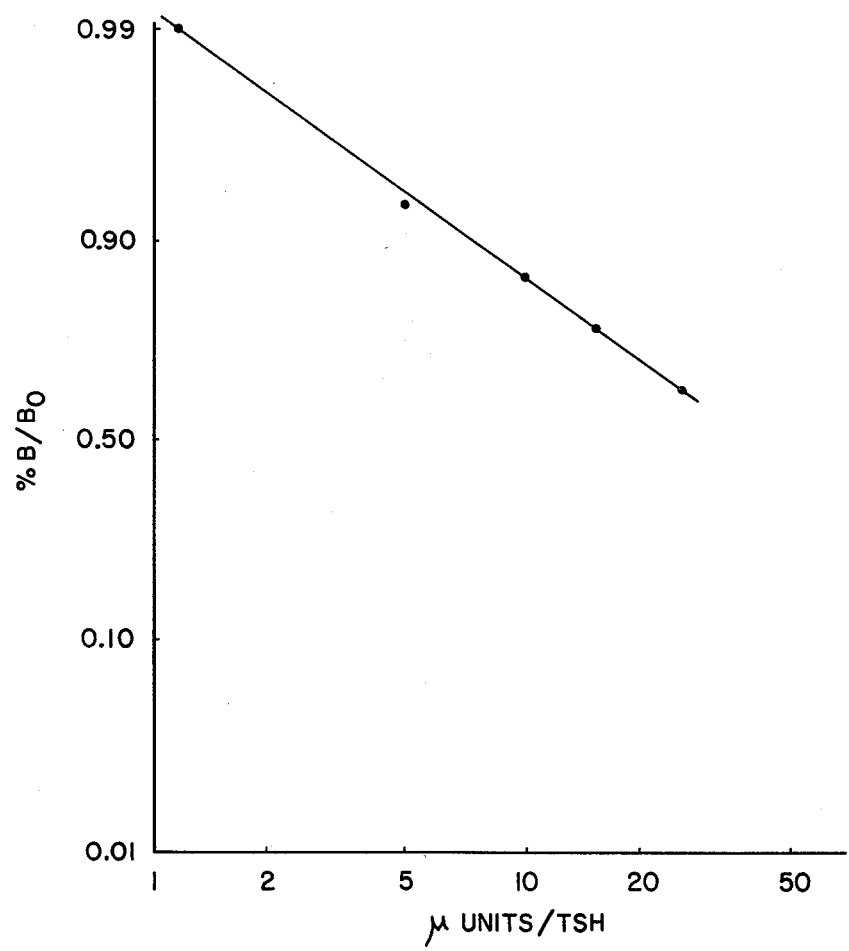
FIG. 5 is a graphical representation of a typical standard curve obtainable in performing assays according to the present method, the particular standard curve shown being that for an assay to determine the ligand thyroid stimulating hormone (TSH) in serum as described in the Examples.

A standard curve was obtained by plotting the $\%B/B_o$ values of standard reference samples versus the corresponding concentrations of TSH [in microunits ($\mu$U) per milliliter (ml)] on a log-logit paper. A unit of TSH is defined as $10^{-4}$ gram. The curve is shown in FIG. 5 of the accompanying drawings.

Unknown amounts of TSH, e.g., in human serum, can be determined in the above manner with the aid of the standard curve. Using the standard curve, three reference sera obtained from Dade Reagents, Miami, Florida USA were tested in duplicate. The results obtained were as follows:

Serum No. 1:
  Expected value—4.5 $\mu$U/ml;
  Found—4.3 $\mu$U/ml.
Serum No. 2:
  Expected value—8.5 $\mu$U/ml;
  Found—8.2 $\mu$U/ml.
Serum No. 3:
  Expected value—29 $\mu$U/ml;
  Found—26 $\mu$U/ml.

EXAMPLE 2

Triiodothyronine ($T_3$) Uptake Radioassay

The $T_3$ uptake test assesses the number of free binding sites available on the thyroxine binding globulin (TBG) in serum, which in normal serum inversely reflects the concentration of total thyroxine ($T_4$) in the serum. For performing a $T_3$ uptake test, radioactively labeled $T_3$ is added to a sample of the serum and combines with the available free sites on the TBG. The free-species is separated from the bound-species of the radioactively labeled $T_3$ and the radioactivity of the free-species is selectively counted ("partial count"). For clinical evaluation the result is, as a rule, expressed as the "$T_3$ Uptake Ratio", being the ratio between the partial count of the unknown sample and the partial count of a sample of standard normal serum.

For performing a $T_3$ uptake test according to the present invention, the following reagents were added to a test tube:

1. 200 μl of $^{125}$I-T$_3$ dissolved in citric acid buffer (pH 5.0); and
2. 20 μl of a serum sample or a reference standard sample (standard samples were reconstituted by dissolving in 1.0 ml of distilled water).

The test tube was gently swirled in order to mix the reagents. No incubation period was required. A column test device was prepared as described above, comprising silica gel 60 powder, 230–400 mesh (particle size 0.04–0.0063 mm) as the selective adsorbent in the lower layer and flint powder, (about 100–200 mesh; obtained from Daneflint, Denmark) as the inert particulate filler material in the upper layer, was placed in the test tube and allowed to absorb the entire reaction mixture (about 2 minutes). Immediately thereafter 600 μl of the citric acid buffer was added to the test tube and allowed to be absorbed by the column (about 8 minutes).

The test tube containing the column was placed in a well of a gamma-counter and the radioactivity of the intake portion of the column was selectively measured to obtain the "partial count" of the sample. The T$_3$ uptake ratio was calculated using the formula:

$$T_3 \text{ Uptake Ratio} = \frac{\text{partial count of serum sample}}{\text{partial count of reference sample}} \times$$
(ratio value of reference sample against normal serum)

The results obtained with several clinical sera samples in the low, normal and high ranges are summarized in the following table:

| Range | Expected Values | Values Obtained | Coefficient of Variation* (percent) |
|---|---|---|---|
| Low | 0.616 | 0.575 | 3.80 |
|  | 0.808 | 0.748 | 5.10 |
| Normal | 0.947 | 0.880 | 4.01 |
|  | 0.971 | 0.977 | 3.92 |
| High | 1.40 | 1.428 | 5.71 |
|  | 1.45 | 1.693 | 5.17 |

*based on 20 runs

EXAMPLE 3

T$_3$ Uptake Radioassay

The radioassay described in Example 2 was repeated using a column test device comprising silica gel 60 powder, 230–400 mesh (particle size 0.04–0.0063 mm) as the selective adsorbent in the lower layer, sand as the inert particulate filler material in a middle layer, and a sawdust plug as an upper compression layer (see FIG. 3). The results were calculated as in Example 2 and were as follows:

| Range | Expected Values | Values Obtained | Coefficient of Variation* (percent) |
|---|---|---|---|
| Low | 0.5–0.6 | 0.567 | 5.84 |
| Normal | 0.8–1.0 | 0.900 | 3.38 |
| High | 1.2–1.6 | 1.3 | 2.7 |

*based on 20 runs

EXAMPLE 4

Comparative Data

In order to demonstrate the improved performance of the present method compared to the prior art ascending column chromatography technique the following experiment was performed based on a T$_3$ uptake radioassay.

A prior art column test device was prepared in which the entire column was packed with silica gel powder to give a conformation as shown in FIG. 1. A column test device of the present invention was prepared in which the lower 1 cm of the column comprised silica gel powder and the remaining column was comprised of sand to give a conformation as shown in FIG. 2. Three assay runs were conducted:

1. Control with prior art device—A control run was made wherein 200 μl of $^{125}$I-T$_3$ solution was absorbed into a prior art device followed by 400 μl of water.
2. Assay run with prior art device—200 μl of $^{125}$I-T$_3$ and 20 μl of a serum sample were absorbed into a prior art device followed by 400 μl of water.
3. Assay run with present device—200 μl of $^{125}$I-T$_3$ and 20 μl of a serum sample were absorbed into a device of the present invention followed by 250 μl of water.

After all of the liquid had been absorbed into the columns, they were frozen and cut into 1 cm sections which were separately measured in a gamma counter. The results were as follows:

| Section of Column, in cm's from bottom | Prior Art Device | | Present Device |
|---|---|---|---|
|  | control (kcpm) | assay (kcpm) | assay (kcpm) |
| 1 | 159.0 | 11.9 | 23.8 |
| 2 | 53.0 | 11.3 | 2.5 |
| 3 | 5.0 | 11.6 | 2.7 |
| 4 | 2.0 | 11.3 | 3.9 |
| 5 | — | 8.1 | 7.0 |
| 6 | — | 11.0 | 23.0 |
| 7 | — | 11.3 | 30.8 |
| 8 | — | 34.9 | 32.8 |
| 9 | — | 60.8 | 91.7 |
| 10 | — | 76.1 | — |

Thus, it can be seen that the prior art device failed to effectively separate the adsorbed species from the nonadsorbed species due to "trailing" from the 2nd to the 5th centimeter of the column, yielding kcpm's around 11 along this entire length. On the other hand, the kcpm's in the same length of the present device were around 3 with a kcpm in the 1st centimeter of 23.8, indicating a clear separation and insignificant "trailing".

What is claimed is:

1. In a specific binding assay method for determining a ligand in, or the ligand binding capacity of, a liquid medium,
    wherein for determining said ligand, said liquid medium is combined with assay reagent means comprising (i) as labeled component, said ligand or a binding analog thereof incorporated with a label and (ii) a binding agent for said ligand; or wherein for determining the ligand binding capacity of said liquid medium suspected of containing a binding agent for said ligand, said liquid medium is combined with assay reagent means comprising, as labeled component, said ligand or a binding analog thereof incorporated with a label;
    thereby to form a binding reaction mixture having a bound-species as said labeled component bound to said binding agent and a free-species as said labeled component not bound to said binding agent;

wherein said bound-species and said free-species of said labeled component are separated by contacting at least a portion of said binding reaction mixture, a predetermined time after formation thereof, with a column comprising a bed of an adsorbent material which is both (a) selective for binding one of said bound-species and fre-species and (b) capillarily absorbent relative to said reaction mixture, whereby said at least a portion of said reaction mixture is drawn into said column by capillary action and said bound-species and said free-species are separated along said column; and wherein said label is measured in one of the separated species;

the improvement wherein said column comprises at least one additional bed of material which is capillarily absorbent relative to said reaction mixture, such additional bed being disposed in said column in contact with the end of said adsorbent bed opposite that which is contacted with said reaction mixture, and said additional bed material being substantially nonadsorbent relative to the one of said bound-species and free-species which said adsorbent bed selectively binds.

2. The method of claim 1 wherein said additional absorbent bed is homogeneous throughout its volume.

3. The method of claim 2 wherein said absorbent bed is composed of a particulate material.

4. The method of claim 1 wherein said additional absorbent bed material is substantially nonadsorbent for both of said bound-species and free-species of said labeled component.

5. The method of claim 4 wherein said column comprises a further additional bed of material which is capillarily absorbent relative to said reaction mixture, such further additional bed being disposed in said column in contact with the end of said substantially nonadsorbent bed opposite that which is in contact with said adsorbent bed, and said further additional bed material being adsorbent for the one of said bound-species and free-species which said adsorbent bed does not selectively bind.

6. The method of claim 1 wherein said additional absorbent bed material is adsorbent for the one of said bound-species and free-species which said adsorbent bed does not selectively bind.

7. The method of any of claims 1-6 wherein said label is radioactive.

8. The method of claim 7 wherein said radioactive label is a gamma-emitting substance.

9. The method of any of claims 1-6 wherein the volume of all capillarily absorbent beds in said column is sufficiently large to allow capillary absorption of all of said reaction mixture.

10. The method of claim 9 wherein after all of said reaction mixture has been drawn into said column, the end of said column that contacted said reaction mixture is contacted with a volume of liquid inert with respect to the selective adsorption of said one of said bound-species and said free-species by said adsorbent bed, and said inert liquid is drawn into said column by capillary action to enhance the separation of said species along said column.

11. The method of claim 1 wherein said ligand is selected from the group consisting of antigens and antibodies thereto; haptens and antibodies thereto; and hormones, vitamins, metabolites and pharmacological agents, and their receptors and binding substances.

12. The method of claim 1 for determining said ligand wherein said ligand is an antigen or hapten and said binding agent is an antibody.

13. The method of claim 12 wherein said ligand is thyroid stimulating hormone.

14. The method of claim 13 wherein said adsorbent bed is composed of silica gel and said additional bed is composed of sand.

15. The method of claim 1 for determining said ligand binding capacity wherein said ligand is a thyroid hormone.

16. The method of claim 15 wherein said thyroid hormone is triiodothyronine.

17. The method of claim 16 wherein said adsorbent bed is composed of silica gel and said additional bed is composed of particulate flint.

18. A device for separating the bound- and free-species forms of a labeled component produced in the course of performing a specific binding assay method for determining a ligand in, or the ligand binding capacity of, a liquid medium, which device comprises an elongated tube, liquid permeable retainer means covering one end of said tube, and a column of material which is capillarily absorbent relative to said liquid medium contained within said tube and in contact with said retaining means, said column comprising (i) a first bed of capillarily absorbent material disposed adjacent to said retainer means, the material in said first bed being selectively adsorbent for one of said bound-species and free-species, and (ii) at least one additional bed of capillarily absorbent material disposed in contact with the end of said first bed opposite that which is adjacent to said retainer means, the material in said at least one additional bed being substantially nonadsorbent relative to the one of said bound-species and free-species which said first bed selectively binds.

19. The device of claim 18 wherein said adsorbent first bed and said additional bed are homogeneous throughout their respective volumes.

20. The device of claim 19 wherein said adsorbent first bed and said additional bed are composed of particulate materials.

21. The device of claim 18 wherein said additional bed material is substantially nonadsorbent for both of said bound-species and free-species of said labeled component.

22. The device of claim 21 wherein said column comprises a further additional bed of material which is capillarily absorbent relative to said reaction mixture, such further additional bed being disposed in said column in contact with the end of said substantially nonadsorbent bed opposite that which is in contact with said adsorbent bed, and said further additional bed material being adsorbent for the one of said bound-species and free-species which said adsorbent bed does not selectively bind.

23. The device of claim 22 comprising a gas permeable retainer means covering the other end of said tube.

24. The device of claim 23 wherein said further additional bed is composed of a compressible material compressed between said gas permeable retainer means and said column.

25. The device of claim 18 wherein said additional absorbent bed material is adsorbent for the one of said bound-species and free-species which said adsorbent bed does not selectively bind.

26. The device of claim 18 for use when said label is radioactive, wherein said tube is made of a radiotransparent material.

27. The device of claim 18 wherein the volume of said column is sufficiently large to allow capillary absorption of all of said liquid medium.

28. The device of claim 18 comprising a gas permeable retainer means covering the other end of said tube.

29. The device of claim 28 comprising a further additional bed, such bed being composed of a compressible material compressively interposed between (a) the end of said substantially nonadsorbent bed opposite that which is in contact with said adsorbent bed and (b) said gas permeable retainer means.

30. The device of claim 18 comprising an indicator composition incorporated in at least a minor portion of said column of capillarily absorbent material at the end thereof opposite that which is adjacent to said liquid permeable retainer means, said indicator composition providing a detectable response upon contact with said liquid medium to signal completion of capillary absorption thereof into said column.

31. The device of claim 30 wherein said indicator composition comprises a pH sensitive chromogen to provide a color change upon contact with said liquid medium.

32. The device of claim 18 wherein said adsorbent bed is composed of silica gel and said additional bed is composed of sand.

33. The device of claim 18 wherein said adsorbent bed is composed of silica gel and said additional bed is composed of flint.

34. A test kit for determining a ligand in a liquid medium, comprising, in a packaged combination,
 (a) one or more containers holding
  (1) said ligand or a binding analog thereof incorporated with a label, and
  (2) a binding agent for said ligand, and
 (b) the test device of claim 18.

35. The test kit of claim 34 for determining thyroid stimulating hormone wherein said binding agent is an antibody to thyroid stimulating hormone and wherein, in said test device, said adsorbent bed is composed of silica gel and said additional bed is composed of sand.

36. A test kit for determining the ligand binding capacity of a liquid medium, comprising, in a packaged combination,
 (a) a container holding said ligand or a binding analog thereof incorporated with a label, and
 (b) the test device of claim 18.

37. The test kit of claim 36 for determining triiodothyronine uptake wherein, in said test device, said adsorbent bed is composed of silica gel and said additional bed is composed of flint.

* * * * *